United States Patent [19]

Prota et al.

[11] Patent Number: 5,704,949
[45] Date of Patent: Jan. 6, 1998

[54] PROCESS FOR THE MANUFACTURE OF A HAIR DYE PRODUCT CONTAINING 5,6-DIHYDROXYINDOLE

[75] Inventors: Giuseppe Prota, Naples, Italy; Gottfried Wenke, Woodbridge; Leszek Wolfram, Stamford, both of Conn.

[73] Assignee: Clairol Incorporated, New York, N.Y.

[21] Appl. No.: 603,953

[22] Filed: Feb. 16, 1996

[51] Int. Cl.$^6$ .................................................. A61K 7/13
[52] U.S. Cl. ........................................ 8/423; 8/406; 548/508
[58] Field of Search ..................... 8/405, 406, 423; 548/469, 508

[56] References Cited

U.S. PATENT DOCUMENTS

| | | | |
|---|---|---|---|
| 4,776,857 | 10/1988 | Carroll et al. | 8/406 |
| 4,808,190 | 2/1989 | Grollier et al. | 8/423 |
| 4,888,027 | 12/1989 | Grollier et al. | 8/423 |
| 4,900,326 | 2/1990 | Grollier | 8/409 |
| 5,173,085 | 12/1992 | Brown et al. | 8/405 |
| 5,273,550 | 12/1993 | Prota et al. | 8/406 |
| 5,279,617 | 1/1994 | Prota et al. | 8/406 |
| 5,279,618 | 1/1994 | Prota et al. | 8/406 |
| 5,435,810 | 7/1995 | Prota et al. | 8/406 |
| 5,441,542 | 8/1995 | Prota et al. | 8/406 |
| 5,486,619 | 1/1996 | Wenke et al. | 548/508 |
| 5,492,541 | 2/1996 | Murphy et al. | 8/423 |
| 5,516,916 | 5/1996 | Murphy et al. | 548/509 |

OTHER PUBLICATIONS

Nature, "Synthesis of 5,6-Dihydroxyindole Derivatives: an Oxio-reduction Rearrangement Catalyzed by Zinc Ions," Harley-Mason et al., pp. 1036–1037, Dec. 1950.

J. Chem. Soc., "Melanin and Its Precursors. Part III. New Synthesis of 5,6-Dihydroxyindole and its Derivatives," Bu'Lock et al., pp. 2248–2252, 1951 (no month avail.).

Gazzetta Chimica Italiana, "A Re-examination of the Zinc-Catalyzed Rearrangement of Dopachrome Using Immobilized Tyrosinase," Napolitano et al., p. 357, 1985 (no month avail.).

Biochem. Biophys. Acta., "Effect of Metal Ions on the Rearrangement on Dopachrome," Palumbo et al., pp. 203–209, 1987 (no month avail.).

Analytical Biochemistry, "Preparation of Eumelanin-Related Metabolites 5,6-Dihydroxyindole, 5,6-Dihydroxyindole-2-carboxylic Acid, and Their o-Methyl Derivatives," Wakamatsu et al., pp. 335–340, 1988 (no month avail.).

*Primary Examiner*—Paul Lieberman
*Assistant Examiner*—Caroline L. Dusheck
*Attorney, Agent, or Firm*—Charles J. Zeller

[57] ABSTRACT

The present invention is directed to the preparation of an aqueous hair dyeing composition containing an effective hair dyeing amount—at least 2 mg/ml—5,6-dihydroxyindole (DHI). An aqueous hair dyeing composition is produced by reacting under essentially anaerobic conditions dopa or a salt thereof with an alkali metal ferricyanide oxidant in an aqueous reaction medium to obtain dopachrome, and permitting the dopachrome to undergo rearrangement in the aqueous medium to form 5,6-dihydroxyindole, said rearrangement being conducted in the substantial absence of oxidant, the aqueous medium being buffered by sufficient buffering agent to maintain a pH of from about 4.5 to about 9 for the reaction medium throughout the series of reactions that take place thereafter, removing the ferrocyanide species present in the aqueous system, and lastly, charging the composition into a suitable container.

11 Claims, No Drawings

PROCESS FOR THE MANUFACTURE OF A HAIR DYE PRODUCT CONTAINING 5,6-DIHYDROXYINDOLE

FIELD OF THE INVENTION

The present invention relates to the use of the melanin precursor 5,6-dihydroxyindole to dye hair. More specifically, the present invention relates to a process for making an aqueous 5,6-dihydroxyindole composition by reacting dopa and ferricyanide oxidant under essentially anaerobic conditions, said composition having a 5,6-dihydroxyindole concentration effective to dye hair. Most specifically, the present invention concerns the manufacture of a ready-to-use dihydroxyindole-containing hair dye product, for example, an aerosol container charged with said composition, that may be purchased by the consumer and applied directly to hair to effect a color change.

BACKGROUND OF THE INVENTION

As reported, for example, in Prota, *Progress in the Chemistry of Melanins and Related Metabolites*, Med. Res. Reviews, 8:525–56 (1988), melanins are naturally occurring pigments present in hair and skin. In humans biosynthesis takes place in tyrosinase-containing melanocytes. The tyrosinase enzyme catalyzes the hydroxylation of tyrosine to dopa and its subsequent oxidation to dopachrome. Once formed, dopachrome undergoes a series of complex reactions in the formation of eumelanins. Eumelanins provide black and brown pigments, and are formed by oxidative polymerization of 5,6-dihydroxyindole derived biogenetically during the melanogenesis.

The metabolite 5,6-dihydroxyindole (DHI) can be made synthetically by a variety of routes, described below in greater detail. Synthetic DHI has been disclosed in the prior art for use in hair and skin dyeing. For example, U.S. Pat. No. 2,934,396 to Charle discloses a process for dyeing hair by contacting hair with an aqueous solution of DHI having a pH of at most 7 for 5 to 60 minutes, followed by an application of an aqueous solution capable of inducing oxidation and/or polymerization of DHI. Similarly, the following patents disclose hair dyeing using DHI:

| | |
|---|---|
| U.S. Pat. No. 3,194,734 | Seemuller et al |
| U.S. Pat. No. 4,804,385 | Grollier et al |
| U.S. Pat. No. 4,808,190 | Grollier et al |
| U.S. Pat. No. 4,822,375 | Lang et al |
| U.S. Pat. No. 4,900,326 | Grollier |
| U.S. Pat. No. 5,173,005 | Brown et al |

Initial investigations into melanogenesis were conducted by Raper, *XIV. The Tyrosinase-Tyrosine Reaction*, Biochem. J., 89–96 (1927). Raper essentially conducted the tyrosinase-catalyzed oxidation of tyrosine in vitro. By terminating the oxidation of tyrosine at the dopachrome stage, Raper was able ultimately to isolate the dimethyl ethers of 5,6-dihydroxyindole, which ethers could not, however, be demethylated to DHI.

Bu'Lock et al, *Melanin and Its Precursors. Part III. New Synthesis of 5:6-Diydroxyindole and its Derivatives*, J. Chem. Soc., 2248–52 (1951), discloses the synthesis of 5.6-dihydroxyindole by oxidation of dopa to dopachrome, followed by subsequent rearrangement and decarboxylation.

The Bu'Lock et al article discloses oxidation often 2-3', 4'-dihydroxyphenylethyl amine derivatives, including dopa. For methyl dopa (described at page 2251), a $4.735 \times 10^{-2}$M concentration of methyl dopa was reacted with a 0.1974M concentration of potassium ferricyanide, in the presence of sodium bicarbonate buffer at a 0.238M concentration. After 10 minutes 8 cc of a 20% zinc acetate solution was added to effect rearrangement of the dopachrome to the dihydroxymethylindole. The article indicates that a similar procedure was used for dopa. The reported 5,6-dihydroxyindole yield of one experiment, after purification, was 30%. However, the Bu'Lock article states that this yield could not be repeated. According to the article the solid light-brown residue obtained in subsequent experiments appeared to be polymeric. At page 2249 Bu'Lock et al hypothesized that their inability to repeat the sole successful experiment was attributable to the diluteness of the reaction medium. This later article by Bu'Lock et al supplements their prior article in Nature, 166:1036–7 (1950), which reported "an excellent yield" of 5,6-dihydroxyindole, and essentially negates their original findings.

Napolitano, et al, *A Re-examination of the Xinc-Catalyzed Rearrangement of Dopachrome Using Immobilized Tyrosinase*, Gaz. Chim. Italiana, 115:357–9 (1985), investigated the zinc ion induced rearrangement process of Bu'Lock et al, using dopachome formed from dopa using tyrosinase catalyst in an aqueous, phosphate-buffered medium. According to Napolitano et al, such zinc ion induced rearrangement of dopachrome solutions at $4 \times 10^{-4}$M concentration leads mainly to 5,6-dihydroxyindole-2-carboxylic acid (DICA), even when the zinc ions are present in low concentration. While the yield of 5,6-dihydroxyindole increases with decreasing zinc ion concentration, the rearrangement time correspondingly increases. Thus, at a 0% zinc ion concentration, a 71% yield of 5,6-dihydroxyindole is obtained after more than 4 hours. At these concentrations of dopa present in the reaction medium, this yield of DHI is too low to be effective as hair coloring vehicle.

In an extension of Napolitano et al, Palumbo et al, *Effect of Metal Ions on the Rearrangement of Dopachrome*. Biochem. Biophys. Acta, 925:203–209 (1987), it was found that the number of transition metal ions exert a profound influence on the kinetics and chemical course of the rearrangement of dopachrome.

Wakamatsu et al, *Preparation of Eumelanin-Related Metabolites 5,6-Dihydroxyindole, 5,6-Dihydroxyindole-2-carboxylic Acid, and Their O-Methyl Derivatives*. Anal. Biochem., 170:335–40 (1988) investigated DHI synthesis by conversion of dopachrome generated in situ by ferricyanide oxidation of dopa. In this synthesis 0.99 g dl-dopa was dissolved in 500 ml (5 m mol) water to which solution was added 6.6 g (20 m mol) of potassium ferricyanide and 2.5 g (30 m mol) sodium bicarbonate in 60 ml water. Notwithstanding the diluteness of the reaction medium (0.01M dopa), the yield was reported as only 40% based on dopa. Again, the DHI concentration is too low to be useful as a hair dyeing agent.

In any event, the syntheses of Raper, Bu'Lock et al, Napolitano et al, Palumbo and Wakamatsu et al all fail to provide a commercially feasible process for making 5,6-dihydroxyindole Moreover, in all instances the concentration of DHI in the aqueous solution after completion of the reaction is too low for such solution to be useful as a hair dye product. This is because the initial dopa concentration was maintained at a very low level to prevent competing reactions. Even so, it is seen that generally low yields of DHI were obtained.

Indeed, these drawbacks in the processes described above, and others, e.g., the catalytic reductive cyclization of 4,5- dihydroxy-2-B-dinitrostyrene disclosed in U.S. 4,555,765 to Murphy, have prevented the use of 5,6-dihydroxyindoles in the dyeing of hair.

Notwithstanding the inability to effect synthesis of 5,6-dihydroxyindole at a reasonable cost, interest in its use in the dyeing of hair remains quite high. This is because DHI and the melanin pigments obtained by its oxidation during the hair treatment process provide extraordinarily natural colors. Moreover, they are not irritating to the skin. Nor are they mutagenic. For all intensive purposes, these synthetically derived compounds behave essentially as those same compounds present in natural hair. Accordingly, an economical process for the preparation DHI in sufficient concentration to dye hair has long been sought after, and would represent a major advance in the art. In particular, a DHI-containing product that was available for use by the consumer as purchased—without mixing of precursors to effect formation of DHI—would be a major advance in the art, owing to its ease of use, availability and suitability for home (rather than salon) hair coloring.

It has now been found, quite surprisingly, that a ready-to-use hair dye product suitable for home use providing an aqueous hair dyeing composition containing an effective hair dyeing amount of 5,6-dihydroxyindole can be made inexpensively using readily available dopa as a starting material.

Accordingly, it is an object of the present invention to provide for the use of the melanin precursor 5,6-dihydroxyindole to dye hair.

It is another object of the present invention to provide for a process for making an aqueous 5,6-dihydroxyindole composition by reacting dopa and ferricyanide oxidant under essentially anaerobic conditions.

Lastly, it is an object of the present invention to provide for a process for the manufacture of a ready-to-use dihydroxyindole-containing hair dye product, which may be purchased by the consumer and applied directly to hair to effect a color change.

These and other objects of the invention will become apparent from the following discussion of the invention.

SUMMARY OF THE INVENTION

The present invention provides for a process comprising the preparation of an aqueous hair dyeing composition containing an effective hair dyeing amount—at least 2 mg/ml—5,6-dihydroxyindole (DHI).

An aqueous hair dyeing composition is produced by reacting, under essentially anaerobic conditions, dopa or a salt thereof with an alkali metal ferricyanide oxidant in an aqueous reaction medium buffered by sufficient buffering agent to maintain a pH of from about 4.5 to about 9 for the reaction medium throughout the series of reactions that take place, as set forth in greater detail below, thereafter removing the ferrocyanide species present in the aqueous system, and lastly charging the composition into a suitable container.

In order to achieve the threshold effective DHI concentration of 2 mg/ml in the aqueous hair dyeing composition, it is critical to obtain a high molar yield of DHI with a high initial dopa concentration in the aqueous reaction medium. Heretofore, these dual requirements have not been deemed achievable due to the fact that substantial DHI yield-reducing competing reactions occur when a high initial dopa concentration is present in the aqueous reaction medium.

Secondly, in accordance with the present invention, the ability to obtain a commercially feasible hair dye product is accomplished by removing ferrocyanide from the reaction media following DHI formation. Ferrocyanide is formed by reduction of the ferricyanide during the oxidation of dopa. Its removal is preferably accomplished by means of precipitation with zinc acetate, thereby removing from the system a reaction product that deleteriously affects the suitability of the final composition for commercial sale.

The advantages of the present invention will be more clearly understood from the following description of the various specific embodiments.

DETAILED DESCRIPTION OF THE INVENTION

As previously stated, the process of the present invention comprises the manufacture of a hair dye product comprising: (a) the preparation of an aqueous hair dyeing composition containing at least 2 mg/ml 5,6-dihydroxyindole, a melanin precursor having the chemical structure:

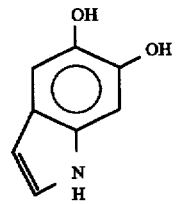

by the oxidation of dopa with an ammonium or alkali metal ferricyanide oxidizing agent in an aqueous reaction medium containing sufficient buffer to maintain the pH of the reaction medium between about 4.5 to about 9 during the reaction; (b) removing ferrocyanide formed during the reaction of step (a), and (c) charging the resulting aqueous hair dyeing composition to a suitable package, said process being conducted in a manner adapted to prevent incorporation of a DHI-depleting concentration of air or other oxidizing contaminant into the final hair dye product composition. Preferably, the entire process is conducted anaerobically.

The 2 mg/ml DHI concentration is the minimum effective or threshold level which has been found to be necessary to achieve a reasonably useful coloring of hair within an acceptable period of time following application of the composition to the hair. Below this concentration some coloring to the hair may be detected visually or by standard analytical methods in the field. But the coloring is too weak to be useful in the hair coloring field, even when melanogenesis is catalyzed by a transition metal cation such as copper, as is know in the art. The catalysis of the hair dyeing procedure by means of a transition metal cation is discussed below. Typically, the DHI concentration in the composition is from about 2 to about 15 mg/ml, preferably from about 4 to about 12 mg/ml, most preferably from about 8 to 12 mg/ml. The contact time for the composition on the hair is from about 5 to about 60 minutes. A longer contact time is necessary when the DHI concentration in the composition is proximate the 2 mg/ml threshold level. At the preferred DHI concentration levels, the contact time would be, typically, from about 5 to about 30 minutes.

It should also be understood that a suitable aqueous hair dyeing composition can be obtained from the aqueous reaction medium and without adding additional ingredients. However, other ingredients, e.g., thickener, surfactant, etc., are generally incorporated to enhance the elegance of the product.

In the process of the present invention, two equivalents of the ferricyanide oxidant oxidize dopa to dopaquinone which spontaneously forms cyclodopa. Two additional mole equivalents of the oxidant react with the cyclodopa to form dopachrome, a readily observed intermediate in the complete sequence of reactions. Dopachrome undergoes spontaneous, although not immediate, transformation to 5,6-dihydroxyindole through rearrangement of the dopachrome species and the release of carbon dioxide. The reactions for the preparation of DHI are presented below.

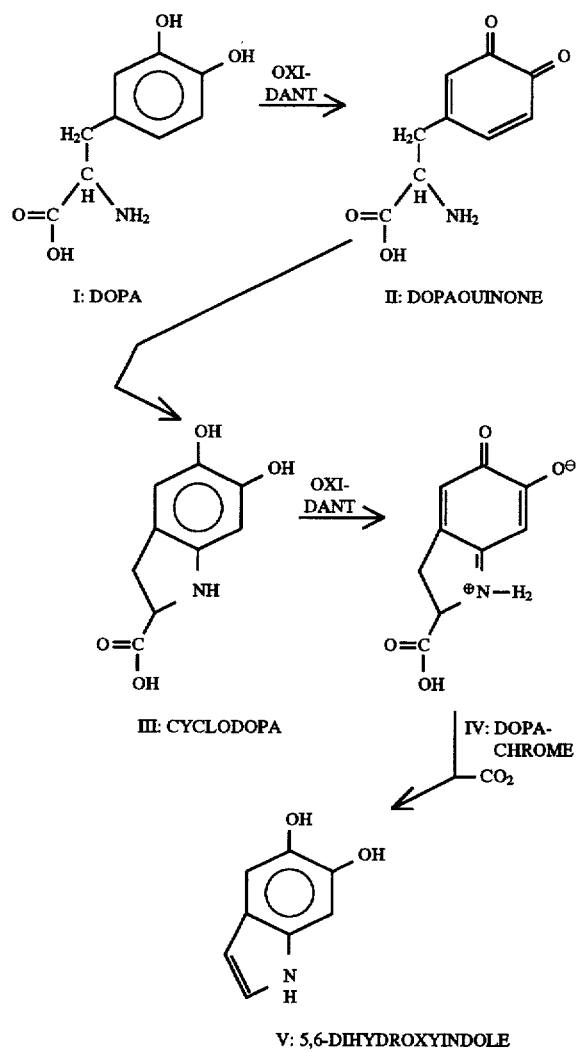

It is seen that the sequence of reactions above is conducive to many possible competing reactions. Thus, dopachrome may also rearrange to form 5,6-dihydroxyindole-2-carboxylic acid, a less useful melanin precursor in the hair dyeing field. Other melanin precursors are also formed, but in minor amounts. In particular, it is seen that any species that reacts with dopachrome will seriously reduce the yield of DHI obtained. On the other hand, it is necessary to ensure that the DHI present in the aqueous composition is at an effective hair dyeing amount, without further concentration of the DHI in the composition after its formation by, for example, evaporation. Accordingly, there should be sufficient oxidant present in the reaction medium at the outset to oxidize all of the dopa initially present to dopachrome.

It has been found that the ferricyanide oxidant reacts with the dopa initially present in the reaction medium and with the cyclodopa formed in the reaction medium rapidly. Thus, the four equivalents of the oxidant are substantially consumed before an appreciable concentration of dopachrome is obtained. As a result, most of the dopachrome formed by the reaction is available for rearrangement to DHI (or to the other melanin precursors in minor amounts). Accordingly, high molar yields of DHI are obtained in the step (a) of the process of the present invention. It has also been found that the initial dopa concentration in the reaction medium can be high—up to the solubility limit of the dopa or dopa salt species employed—without serious diminution in DHI molar yield.

It should be understood that the ability to obtain the threshold-effective DHI concentration depends on both the DHI yield and the amount of dopa available for conversion. Thus, a lower DHI yield would be acceptable when a high initial dopa concentration is provided in the reaction medium. Conversely, a high DHI yield would need to be achieved if a low initial dopa concentration is used. The initial dopa concentration in the reaction medium is at least about 2.5 mg/ml, a molar yield of about 93% DHI based on dopa being necessary to obtain the threshold level at this initial dopa concentration. More typically, the initial dopa concentration is in the range of 3 to 6 mg/ml, with DHI yields cooperatively being between about 80 to 40%, in order to achieve the threshold effective DHI level in the aqueous composition.

Preferably, however, the DHI concentration in the aqueous composition is from about 4 to about 12 mg/ml, with DHI molar yields being from about 50 to about 70% and initial dopa concentrations in the reaction medium being from about 6 mg/ml to the solubility limit of the dopa species employed at the pH used.

To achieve the higher DHI concentration in the aqueous composition at modest yields between 60 and 75% molar conversion of dopa to DHI, it is generally necessary that the initial dopa concentration in the reaction medium be well above the water solubility limit of dopa. An acid or alkaline aqueous solution of dopa is, therefore, typically used for preparation of the aqueous reaction medium. Alternately, the more soluble dopa acid or basic salts can be used in the preparation of the reaction medium. Use of the dopa salt or the use of an acid or alkaline dopa premix allows the otherwise relatively insoluble dopa to go into solution and be available for reaction.

Illustrative of the suitable acid salts of dopa are dopa hydrochloride and dopa sulfate. Dopa hydrochloride is preferred. Among the suitable basic salts of dopa that can be used are the alkali metal salts and the alkaline earth metal salts of dopa. The sodium and potassium salts are preferred. Any inorganic or organic acid or base can be used to adjust the pH of the dopa premix solution, provided that the agent used does not interfere in the reactions. Sodium hydroxide and hydrochloric acid are preferred.

In conducting the preparation of the aqueous hair dyeing composition, it is critical to maintain the pH of the reaction medium between 4.5 to 9 during the dopa oxidation and dopachrome rearrangement reactions. Preferably, the pH is between 6 and 8. Inasmuch as the pH of the reaction medium will fall during the reactions, it is necessary to provide a sufficient amount of a buffering agent in the reaction medium to maintain the requisite pH. Suitable buffering agents are the alkali metal salts of phosphates, carbonates, bicarbonates and borates. Also suitable are aminic buffers, such as N-[2-hydroxyethyl]-piperazine-N'-[2-ethanesulfonic acid] (HEPES), N-[2-acetamido]-2-aminoethane sulfonic acid (ACES), tris[hydroxymethyl] aminomethane (TRIZMA) and N-tris[hydroxy-methyl]-methyl-3-aminopropane sulfonic acid (TAPS). The ammonium and alkali metal carbonates and bicarbonates are suitable, even though not typically employed as buffers in the stated pH range. The preferred buffers used in the practice of the present invention are sodium and potassium carbonate, bicarbonate or phosphate. Other buffers suitable for maintaining reaction medium pH and to potentiate the rearrangement may exist which may be determined by simple experimentation, as herein disclosed in the examples. The buffers may be present in an amount in excess of that required for maintenance of the reaction medium pH.

Because (i) ferricyanide rapidly oxidizes dopa to dopachrome, (ii) ferricyanide is provided in essentially stoichiometrically correct concentration, and is, therefore, essentially depleted prior to the onset of the dopachrome rearrangement, and (iii) the ferrocyanide obtained by reduction of ferricyanide is a nonoxidizing species, the rearrangement reaction rate is not critical. Normally, dopa is provided in slight excess over the ferricyanide stoichiometric requirement so as to ensure that all of the ferricyanide present reacts. A stoichiometric equivalent ratio of dopa to ferricyanide of about 1.25:1 to 1.01:1, preferably 1.05.1 to 1.01:1, is provided. The reaction time for the rearrangement is normally not less than 30 minutes and not greater than three hours, depending on the size of the batch, concentration of the dopachrome in the reaction medium, batch temperature, reaction medium pH, and the like. Preferably, the rearrangement is conducted in from 45 to 90 minutes, which provides suitable time for batch handling, as described below, without unduly increasing equipment size.

The dopachrome rearrangement reaction is conducted under oxygen-free conditions. This is because DHI is readily oxidized by oxygen to form melanin, which is not suitable for dyeing hair once it is formed as it does not penetrate into the hair cortex. Such anaerobic conditions can be achieved by conventional means. For example, a kettle type reactor may be blanketed with a nonoxidizing gas such as nitrogen, carbon dioxide, argon, and the like. Reactors which are completely liquid-filled, such as plug flow reactors, are also oxygen-free, and may be used in this reaction step. Generally, it is highly desirable to also conduct the dopa and dopachrome oxidation reactions anaerobically, as these reactions are rapid and incipient dopachrome rearrangement would occur prior to provision of anaerobic conditions for the rearrangement.

Ferrocyanide is removed from the reaction medium following conversion of dopachrome to DHI. Because the ferrocyanide is a colored species, it may cause an undesirable color to the product unless removed. The ferrocyanide or its decomposition products may also create formulating problems. For example, the ability to properly and uniformly thicken the composition batch to batch is made more difficult by the presence of high concentrations of ionic species.

The ferrocyanide may be removed by one of several means. Preferred is the addition of zinc acetate to precipitate zinc ferrocyanide, generally in a 1.5-2:1 molar ratio of Zn acetate to ferrocyanide, however, excess Zn acetate may be used. Preferably an effective amount of Zn acetate will be employed. The resulting precipitate is removed by conventional means, for example, filtration and centrifugation, the latter being preferred. Less preferred, the ferrocyanide may be removed by counter current extraction of DHI from solution with ethyl acetate. Other known extraction methods may also be utilized as will be apparent to those skilled in the art, such as for example ion exchange and crystallization methods.

The final step of the process of the present invention is to charge a suitable container with the ferrocyanide-free, DHI-containing composition. Of the suitable containers, three preferred types can be illustrated.

The first type of container is an aerosol can, the DHI composition and propellant being charged into the aerosol can. Methods for doing so yet preventing entrainment of air are known in the art. For example, by rapidly deaerating the can and then charging with dyeing compositions and propellant gas. Typically, the aerosol product will contain from about 30 to 95%, preferably from about 60 to 85%, propellant by weight of the aqueous DHI composition. Suitable propellants are C3-C5 hydrocarbons, especially isobutane, hydrofluorocarbon 152A and dimethyl ether.

A second type of product incorporates within a suitable container a collapsible bladder filled under pressure with liquid hair dye composition. As product composition is discharged through the outlet nozzle, the bladder contracts maintaining an air-free environment. An example of this type of delivery system is the Excel device.

It is also suitable to prepare the aqueous hair dye composition as a gel or cream, such gel or cream formulations being suitably charged to a squeazeable tube. In this embodiment of the invention, the gel or cream system is essentially anaerobic, ambient air being unable to diffuse substantially into the composition even if the closure cap is inadvertently left off for a period of time. Quite understandably, widemouthed jars and the like are of questionable suitability and are best avoided.

Optional Constituents

The variously described embodiments of the present invention may also include in the hair dye composition one or more optional ingredients. With regard to the products prepared by the consumer, the optional ingredients may be provided in one or more additional containers, or may be, if compatible, incorporated into the solutions previously described. Incorporation of the optional ingredients into the prepared products has been described in the previous section.

Typical optional ingredients include an organic solvent such as ethyl alcohol, isopropyl alcohol or propylene glycol; a thickener such as sodium alginate or gum arabic, or cellulose derivatives, such as methylcellulose, e.g., Methocel 60HG, or the sodium salt of carboxymethylcellulose, or hydroxyethyl-cellulose, e.g., Cellosize QP-40 or acrylic polymers, such as polyacrylic acid sodium salt, or inorganic thickeners, such as bentonite; an anionic or nonionic surfactant to enhance solubilization of the various constituents; a cationic surfactant to condition hair, an emollient for the skin and other ingredients as may be deemed desirable. These optional constituents are provided in an amount to provide their desired function, as conventionally known in the art.

Carboxymethylcellulose is pre-dissolved in water. The DHI-containing solution is added to this pre-mix with stirring. The final concentration of carboxymethylcellulose in the combined solutions is about 2%, with a suitable range being from about 0.5-5%.

Surfactant, for example, sodium lauryl sulfate is added to give a final concentration of about 1%, with suitable range being from about 0.1-30%. Other suitable surfactants are, for example, behenalkonium chloride, didecyldimoniumchloride, sodiummethyloleoyltaurate, sodium laureth sulfate, cocamidopropyl betaine and cocamidopropyl sultaine.

Isopropanol is added to the aqueous DHI-containing solution to give a concentration of about 10% in the final product, with a suitable range being from about 1-30%. Other suitable solvents include ethanol, propanol, alkyl alcohols of 1–6 carbons, glycols of up to about 10 carbons, such as diethyleneglycol, glycol ethers, such as diethyleneglycolmonoethylether, carbitols, benzylalcohol, and similar materials.

Antioxidant, such as for example, sodium dithionite, sodium sulfite, ascorbic acid, and erythorbic acid, is added to the DHI-containing solution to give a final concentration of about 0.5%, with a suitable range being from about 0.01–5%.

Preservative, such as for example, methyl- or propylparaben, 2-phenoxyethanol, DMDMH and Kathon CG, is added to the DHI-containing solution to give a final concentration of about 0.5%, with a suitable range being from about 0.01–5%.

The foregoing list of optional ingredients is not intended as limiting. Other suitable adjuvants for inclusion in the hair dye composition are recited, for example in Zviak, *The Science of Hair Care* (1986) and Balsam and Sagarin, *Cosmetics: Science and Technology*, Vol. 2 (Second Edition 1972).

It is also know that certain metal salts, such as copper, magnesium, titanium and iron salts, accelerate the oxidation of DHI in a hair coloring process. Solutions of these salts are applied to hair in conjunction with the application of the DHI as a pre, post or simultaneous treatment. Accordingly, the kit containing the first and second premixes may also contain a solution of these metal salts.

Suitable for pre-treatment of hair is, for example, a shampoo, containing 2% of coppersulfate and MEA to adjust to a pH of approximately 8. A similar shampoo might be used for a post-treatment of hair after application of DHI.

The metal salts may also be included in a combination package with the prepared hair dyeing compositions, or sold separately for use with the process of the present invention.

The invention is now illustrated by the following examples:

EXAMPLES

Example I 5.1 g DOPA was dissolved in 25 ml 1N HCL and 100 ml of water. The solution was purged with an inert gas (argon or nitrogen) and heated to 45° C.

A second solution was prepared containing 30.6 g potassium ferricyanide, 14.89 g sodiumbicarbonate in 100 ml water. The second solution was purged with an inert gas and added rapidly to the first solution with stirring. The combined solution was heated to approximately 45° C. and stirred in an inert atmosphere for 1 hour. After cooling to ambient temperature, 0.5 g EDtA and 0.5 g erythorbic acid were added. Maintaining the inert atmosphere, 29.99 g zinc acetate were added to the aqueous solution in portions and with continued stirring. A precipitate of zinc ferrocyanide formed rapidly. The DHI-containing solution was separated from the precipitate by centrifugation. The DHI concentration was measured by HPLC.

The DHI-containing solution could be used as such, or after addition of other adjuvents, to dye hair. This is demonstrated in Example 2.

Example II

A tress of gray hair was placed in an aqueous solution, containing 2% copper sulfate and MEA to adjust a pH of ca.9.0. After 5 minutes, the hair tress was rinsed with water and exposed to a DHI-containing solution, prepared as described in Example 1, for 10 minutes. The hair was rinsed, shampooed and dried. The hair was dyed to a black color.

| | Hunter Values | | |
|---|---|---|---|
| | L | a | b |
| before treatment | 38.2 | 0.2 | 7.8 |
| after treatment | 12.3 | 0.3 | 0.2 |

It will be further apparent to one skilled in this art that the improvements provided for in the present invention, while described with relation to certain specific embodiments, also lend themselves to being applied in other embodiments not specifically provided for herein, which are nonetheless within the spirit and scope of the invention taught here.

I claim:

1. A process for the manufacture of a shelf stable hair dye product comprising a container and an essentially air-free hair dye composition containing at least one indolic melanin precursor, the process comprising the steps of:

(a) preparing an aqueous hair dye composition containing the melanin precursor 5,6-dihydroxyindole by (i) reacting dopa and salts thereof with an alkali metal ferricyanide oxidant in an aqueous medium to obtain dopachrome, (ii) permitting the dopachrome to undergo a rearrangement reaction in the aqueous medium to form 5,6-dihydroxyindole, said rearrangement being conducted in the substantial absence of oxidant, the aqueous medium being buffered by a buffering agent suitable to maintain the pH of the aqueous media between about 4.5 to about 9 during the reactions (i) and (ii), and (iii) removing ferrocyanide produced during the reaction (i) and the rearrangement reaction (ii); and (b) charging a container with the aqueous hair dye composition from step (a), said process being conducted under substantially anaerobic conditions to avoid incorporation of oxygen into said hair dye product, said hair dye product having a 5,6-dihydroxyindole concentration of at least 2 mg/ml by weight of the hair dye composition.

2. The process of claim 1 wherein the dopa and oxidant reactants are initially present in the aqueous media in substantially stoichiometric equivalent concentrations required for the reaction of dopa to dopachrome.

3. The process of claim 1 wherein the buffering agent is selected from the group consisting of phosphate, carbonate, bicarbonate and borate salts of sodium or potassium, and aminic buffers selected from the group consisting of N-[2-hydroxyethyl]piperazine-N'-[2-ethanesulfonic acid] (HEPES), N-[2-acetamido]-2-aminoethane sulfonic acid (ACES), tris [hydroxymethyl]aminomethane (TRIZMA) and N-tris[hydroxymethyl]-methyl-3-aminopropane sulfonic acid (TAPS).

4. The process of claim 1 wherein the buffering agent is selected from the group consisting of carbonate and borate salts of sodium and potassium.

5. The process of claim 1 wherein the container is an aerosol can.

6. The process of claim 1 wherein the container is a collapsible bladder.

7. The process of claim 1 wherein the aqueous hair dye composition is in the form of a gel or cream, and the container is a squeezeable tube.

8. The process according to claim 1 wherein the 5,6-dihydroxyindole concentration in the composition upon the completion of the rearrangement reaction is from about 2 to about 15 mg/ml.

9. The process of claim 1 wherein the buffering agent is present in an aqueous medium in an amount in excess of the amount needed to maintain the pH of the reaction medium between about 6 to about 8, and wherein there is an initial slight stoichiometric equivalent excess of dopa to ferricyanide oxidant.

10. The process of claim 1 wherein the ferrocyanide is removed in step (a)(iii) by precipitation with zinc acetate.

11. The process of claim 10 wherein the zinc acetate is present in amount of from about 1.5:1 to 2.1 molar excess of zinc acetate to ferrocyanide.

* * * * *